(12) United States Patent
Thompson et al.

(10) Patent No.: US 9,138,533 B2
(45) Date of Patent: Sep. 22, 2015

(54) ALARM IDENTIFICATION SYSTEM FOR INFUSION SET WHEN INSTALLED IN PUMP ASSEMBLY

(75) Inventors: Loren M. Thompson, Lapeer, MI (US); Robert R. Voltenburg, Jr., Davison, MI (US)

(73) Assignee: CURLIN MEDICAL INC., East Aurora, NY (US)

( * ) Notice: Subject to any disclaimer, the term of this patent is extended or adjusted under 35 U.S.C. 154(b) by 421 days.

(21) Appl. No.: 13/127,528

(22) PCT Filed: Oct. 22, 2009

(86) PCT No.: PCT/US2009/061584
§ 371 (c)(1),
(2), (4) Date: Jul. 13, 2011

(87) PCT Pub. No.: WO2010/053706
PCT Pub. Date: May 14, 2010

(65) Prior Publication Data
US 2011/0264045 A1    Oct. 27, 2011

Related U.S. Application Data

(60) Provisional application No. 61/198,854, filed on Nov. 10, 2008.

(51) Int. Cl.
*A61M 5/142* (2006.01)
*A61B 19/00* (2006.01)
*A61M 5/172* (2006.01)

(52) U.S. Cl.
CPC .............. *A61M 5/142* (2013.01); *A61M 5/172* (2013.01); *A61B 2019/448* (2013.01); *A61M 2205/18* (2013.01); *A61M 2205/332* (2013.01); *A61M 2205/58* (2013.01); *A61M 2205/6063* (2013.01)

(58) Field of Classification Search
CPC ................. A61M 2205/18; A61M 2205/6018; A61M 2205/58; A61M 5/1413; A61M 5/5086; A61M 5/1418; A61M 39/08; A61B 19/44; A61B 2019/448
USPC ........... 604/118, 111, 93.01, 151, 131, 891.1, 604/65–67
See application file for complete search history.

(56) References Cited

U.S. PATENT DOCUMENTS 4,551,133 A    11/1985   Zegers de Beyl et al.
4,846,792 A     7/1989   Bobo, Jr. et al.
(Continued)

FOREIGN PATENT DOCUMENTS

EP        0960627 A2    12/1999

*Primary Examiner* — Matthew F DeSanto
(74) *Attorney, Agent, or Firm* — Hodgson Russ LLP

(57) ABSTRACT

Disclosed herein is an identification system for an infusion set when the infusion set is installed in a pump. The identification system includes a pump, at least one sensor, a catheter, a tube and an alarm. The pump includes at least one sensor disposed thereon, which is in communication with the alarm. The catheter includes a distal end adapted for insertion into a body, and a proximal end opposite the distal end. The tube is operatively configured at a first end to removeably attach to the proximal end of the catheter, and the tube further includes a second end proximate to the sensor(s) on the pump. The sensor(s) are operatively configured to receive a signal generated at the first end or along a length of the tube, and to trigger the alarm upon receiving the signal so as to identify the corresponding pump.

1 Claim, 2 Drawing Sheets

(56) References Cited

U.S. PATENT DOCUMENTS

| | | | |
|---|---|---|---|
| 5,116,203 A * | 5/1992 | Natwick et al. | 417/53 |
| 5,356,378 A * | 10/1994 | Doan | 604/65 |
| 5,522,799 A * | 6/1996 | Furukawa | 604/65 |
| 6,475,180 B2 | 11/2002 | Peterson et al. | |
| 2006/0265246 A1 * | 11/2006 | Hoag | 705/2 |
| 2007/0060785 A1 | 3/2007 | Freeman et al. | |
| 2007/0083153 A1 | 4/2007 | Haar | |
| 2008/0108942 A1 * | 5/2008 | Brister et al. | 604/118 |
| 2009/0149810 A1 * | 6/2009 | Ring et al. | 604/111 |

* cited by examiner

ALARM IDENTIFICATION SYSTEM FOR INFUSION SET WHEN INSTALLED IN PUMP ASSEMBLY

CROSS REFERENCE TO RELATED APPLICATION

This application claims the benefit of U.S. Provisional Patent Application Ser. No. 61/198,854 for an IDENTIFICATION SYSTEM FOR INFUSION SET WHEN INSTALLED IN PUMP ASSEMBLY, filed on Nov. 10, 2008, which is hereby incorporated by reference in its entirety. This claim is made under 35 U.S.C. §119(e); 37 C.F.R. §1.78; and 65 Fed. Reg. 50093.

TECHNICAL FIELD OF INVENTION

The present disclosure relates generally to an identification system for an infusion set when the infusion set is installed in a pump assembly.

BACKGROUND

Patients who receive intermittent or continuous doses of medication, such as insulin, via subcutaneous injection, often have an infusion set affixed to their skin in a convenient location. Means for keeping an infusion set fixed in place are often discreet and reduce the need for repeated puncturing of the skin with a needle, thereby reducing the risk of infection as well as reducing the formation of scar tissue. An infusion set typically includes a housing which supports a tubular cannula with a removable injection needle at one end for penetrating the skin and a septum at the other end for receiving a needle. The needle is attached to a supply tube from a medicinal source or infusion pump such as, but not limited to, an insulin pump.

The infusion pump infuses fluids, medication, or nutrients into a patient's circulatory system. Some infusion pumps are used intravenously, although subcutaneous, arterial, and epidural infusions are occasionally used. Infusion pumps advantageously enhance methods for administering fluids to patients. As non-limiting examples, an infusion pump can administer as little as 0.1 mL per hour injections, or it can administer fluids to a patient where the volumes may vary depending on the time of day, or in yet another scenario, it can administer up to a maximum number of doses per hour.

U.S. Patent Application No. 61/198,226 discloses is a visual identification system for an infusion set when the infusion set is installed in a pump. The visual identification system includes a pump having at least one colored light source, a tube including a surface, and a catheter. The at least one colored light source is operatively disposed in the pump. The tube has first and second ends, and the surface is configured i) to have light from the at least one colored light source incident thereon and ii) to redirect the incident light through the tube. The catheter has a distal end configured for insertion into a body and a proximal end configured to remain external to the body and to be removably attached to the first end of the tube. The redirected incident light through the tube identifies the catheter to the pump.

While a visual identification system for an infusion set is desirable, it is also desirable to have an alarm system that includes sensor(s) operatively configured to receive a signal generated at the first end or along a length of the tube and to trigger the alarm upon receiving the signal so as to identify the corresponding pump.

SUMMARY

Disclosed herein is an identification system for an infusion set when the infusion set is installed in a pump. The identification system includes a pump, at least one sensor, a catheter, a tube and an alarm. The pump includes at least one sensor disposed thereon, which is in communication with the alarm. The catheter includes a distal end adapted for insertion into a body, and a proximal end opposite the distal end. The tube is operatively configured at a first end to removeably attach to the proximal end of the catheter, and the tube further includes a second end proximate to the sensor(s) on the pump. The sensor(s) are operatively configured to receive a signal generated at the first end or along a length of the tube, and to trigger the alarm upon receiving the signal so as to identify the corresponding pump.

BRIEF DESCRIPTION OF THE DRAWINGS

Features and advantages of embodiment(s) of the present disclosure will become apparent by reference to the following detailed description and drawings, in which like reference numerals correspond to similar components.

DETAILED DESCRIPTION

When implementing an infusion set into a patient, a user attaches a reservoir of the medicine or fluid source to the pump 60. The infusion set is then primed to ensure that there is no air in the system before it is inserted into the patient. The needle of the infusion set is pushed into the layer of fat below the patient's skin, thereby the plastic cannula of the infusion is pushed along with the needle. When the needle is then removed, the cannula is left in place below the skin within the patient.

Many different infusion sets are known. One non-limiting example of such an infusion set is a "straight set," in which the cannula and the injection needle are inserted in an orientation that is substantially normal to the skin. Another traditional infusion set may be referred to as a "low profile angled set" in which the cannula and the injection needle are supported in a housing such that the infusion set is at an acute angle with respect to the skin. Regardless of the type of infusion set used, in some instances, multiple infusion sets with multiple pumps are used on a single patient at once in order to administer the required medicines. The use of multiple infusion sets on a single patient may create some ambiguity in identifying which infusion set corresponds to which medicinal source or pump 60.

Furthermore, a single patient may receive several medicinal therapies at any given time where each medicinal fluid 40 is delivered to the patient with a dedicated pump 60 and disposable infusion set. Often, a working length of up to 100 inches between the pump 60 and the patient may exist, without a systematic routing method to ensure positive matching of the pump 60 to the pump's corresponding infusion set.

Embodiments of the identification system disclosed herein advantageously allow a user to identify which infusion set corresponds to which medicinal source (pump) by creating a mechanical excitation within a tube 10 of the infusion set proximate to the catheter or along a length of the tube 10. The mechanical excitation triggers an audible or visual alarm 55 from the corresponding pump 60 to identify the corresponding pump 60 to the user.

Figure 1:
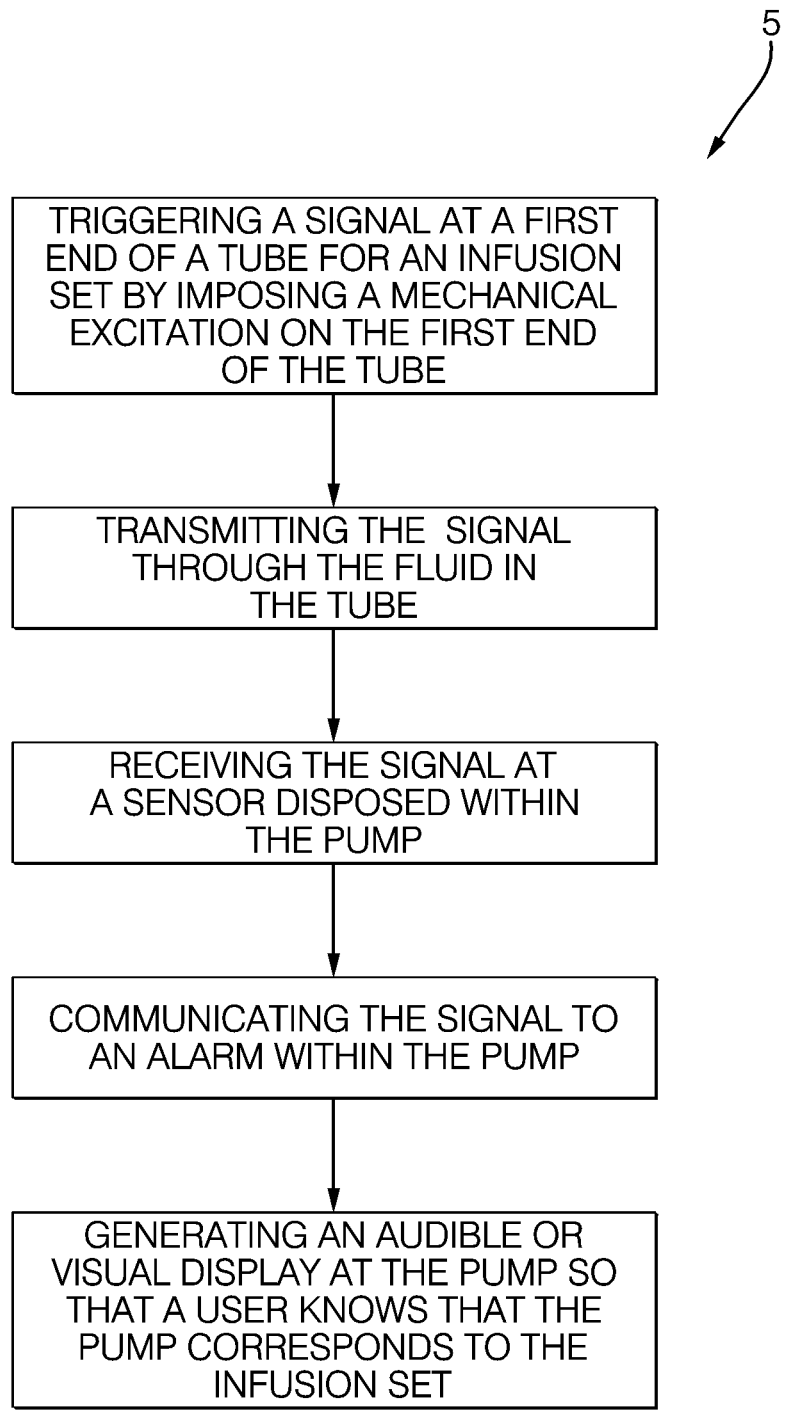
FIG. 1 is a flow chart which illustrates an embodiment of a method for identifying a pump that corresponds with a particular infusion set.

Referring now to FIG. 1, presented in flow chart 5 is an embodiment of the method to identify the pump 60 which corresponds to a particular catheter and tube 10 is shown. Each of the method steps is briefly discussed in reference to FIG. 1, and is described in further detail herein below in reference to FIG. 2. The first step of the method is triggering a signal 30 at a first end, or in some instances, along a length, of a tube 10 for an infusion set by imposing a mechanical excitation on the tube 10, such as fingers 20 squeezing on the tube 10. The method further includes transmitting the signal 30 (or change to the fluid 40 within the tubing) through the fluid 40 in the tube 10. The third step of the method involves receiving the signal 30 at a sensor 50 operatively disposed in or on the pump 60. The fourth step is communicating the signal 30 from the sensor 50 to an alarm 55 in operative communication therewith. The fifth step of the method includes generating an audible or visual display (such as a light or text display on the pump 60 user interface, or the like) at the pump 60 so that a user knows that the pump 60 corresponds to the previously triggered infusion set.

Figure 2:
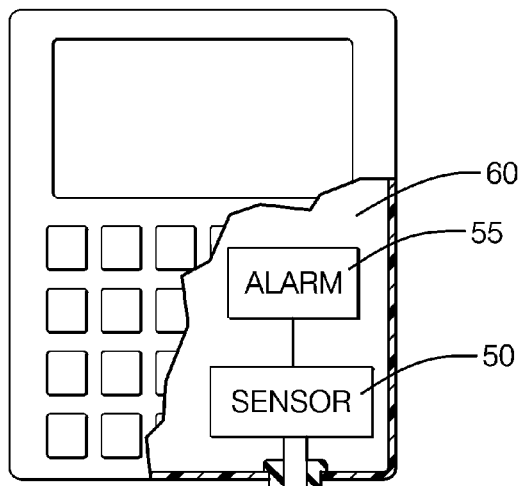
FIG. 2 is a schematic diagram of an embodiment of the identification system of this disclosure, in which a mechanical excitation on the tube is caused by fingers squeezing on the tube.

Referring now to FIG. 2, a pump 60 is shown having a roller assembly (not shown). A non-limiting example of such a pump 60 is a rotary peristaltic pump 60. Such rotary peristaltic infusion pumps may include a removable cassette including the assembly of rollers and a flexible tube 10 that surrounds a portion of the assembly of rollers. As shown in FIG. 2, the flexible tube 10 connects the pump 60 to the catheter. In response to rotational movement of the rollers, portions of the flexible tube 10 in contact with the rollers compress or otherwise occlude against a wall of the cassette. As a result, fluid 40 (i.e., a drug) traveling through the tube 10, which was delivered from a drug container (not shown), is temporarily trapped in the tube 10 between the occluded points. The trapped drug is released from the tube 10 when the occlusion force on the tube 10 is released. In this manner, the drug is urged through the tube 10 via peristaltic wave action and is ultimately delivered to a subject.

While a rotary peristaltic pump 60 is schematically shown and described herein, it is to be understood that other infusion pumps are also suitable for use in the methods of the present disclosure. Examples of such other infusion pumps include syringe pumps and linear peristaltic pumps.

In the embodiment disclosed herein, the pump 60 also includes a sensor 50 disposed thereon. The sensor 50 is capable of resolving a signal 30 such as small vibrations or pressure fluctuations transmitted via the liquid drug or air volume contained within the disposable tubing set. The vibrations required to reach the appropriate threshold for detection by the sensor 50 (such as a pressure sensor, accelerometer, or combinations thereof, or the like) are intentionally imposed on the tubing so that the user is able to identify the pump 60 that is mated to the infusion set (e.g., catheter and associated tubing). The mechanical excitation may be initiated through a variety of means such as, but not limited to: (1) a gentle mechanical strike of the tubing on a hard surface; (2) pressure pulses transmitted to the fluid 40 through human touch of the tubing's elastic surface; (3) a component mechanically attached to the tubing to create a change in pressure within the tubing; or (4) fingers squeezing the tubing. It is also to be understood that a patient's venous pressure pulse may also be used to initiate the vibration within the fluid 40/air when the tubing is connected with a catheter inserted into the patient. This capability enables the pump 60 (thru the sensor 50) to determine the patient's heart rate, the patient's respiratory rate and/or the loss of intravenous connection when the sensor 50 is no longer receiving a signal 30 of the patient's venous pressure pulse.

Figure 3:
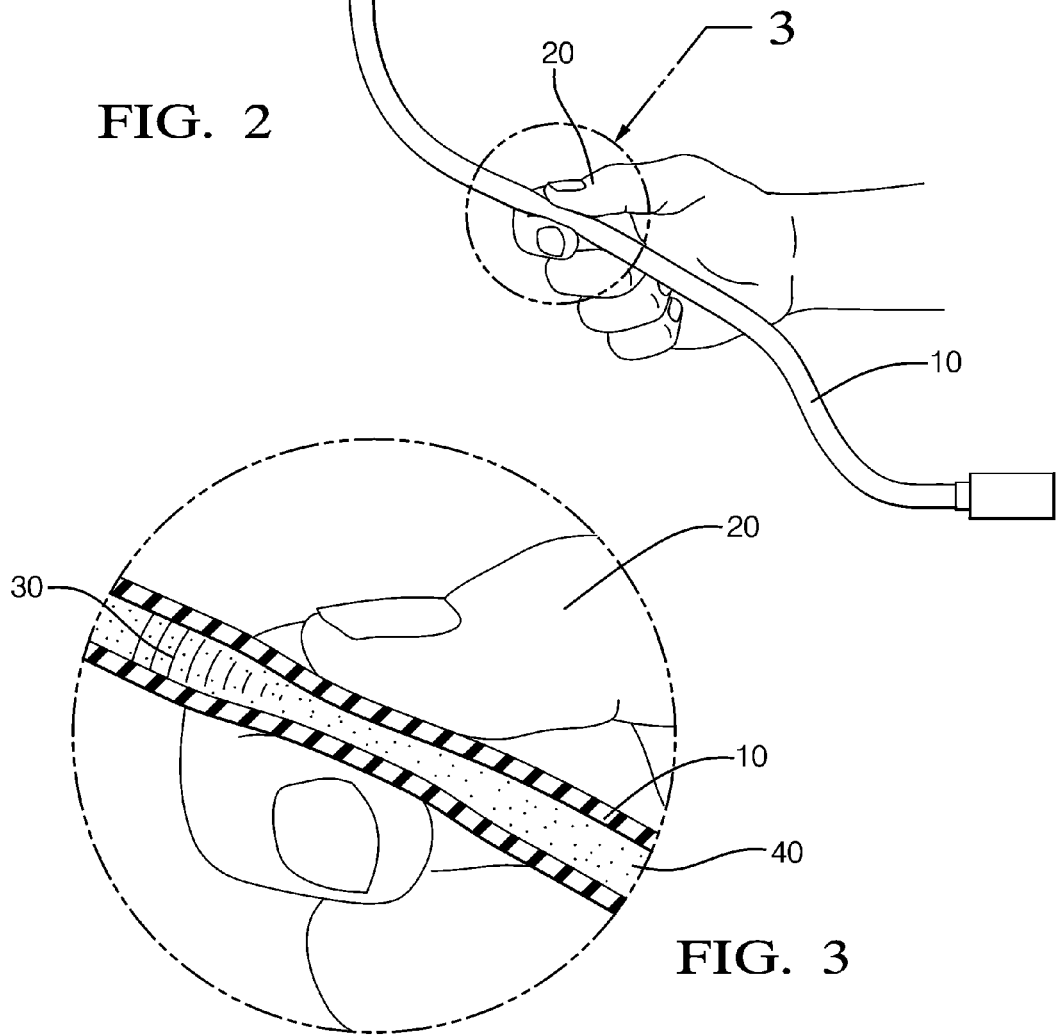
FIG. 3 is a detail view of fingers squeezing the tube to create a mechanical excitation.

Best shown in FIGS. 2 and 3, as the mechanical excitation is initiated on the tubing, the intentional vibration or pressure pulse induced within the tubing is then transfer up through the fluid 40 (liquid or air) in the tubing and is sensed upstream by the sensor 50 which is disposed at the pump 60. The sensor 50, upon recognition of this change in the fluid 40 (whether it is air or liquid), initiates an alarm 55 which indicates to the user which pump 60 is associated with the vibrated tube 10.

It is to be understood that an accelerometer may be used in lieu of, or in conjunction with, a pressure sensor to detect a change within the tubing due to the intentional mechanical excitation. The accelerometer may be useful where there is air in the tubing, and the vibration or pressure change is transferred through the air. The use of an accelerometer in conjunction with a pressure sensor 50 may provide a user with a more sophisticated and fine-tuned level of calibrating and setting the threshold of detection.

The pressure sensor and/or accelerometer may be disposed adjacent to the roller assembly or be part of the roller assembly system. It is to be understood that any positioning of the sensor 50 is suitable as long as the sensor 50 is capable of detecting the change in pressure or movement within the tubing. As such, the aforementioned placement of the pressure sensor 50 and/or accelerometer is intended to be a non-limiting example, and the various means for sensing a change within the tubing may be placed in a variety of locations.

As previously mentioned, the sensor 50, which is responsible for sensing the change within the tubing, is also in communication with the alarm 55 or other signal 30 generating member which may consist of a variety of mechanisms to alert a user. Some non-limiting examples of a signal 30 generating member are: (1) a visual alarm 55 (e.g., a blinking light on the pump 60); (2) an audible alarm 55; (3) readable text on the pump 60 user interface; or (4) combinations of 1, 2 and/or 3.

The tubing used in the embodiments disclosed herein may be, but is not limited to, the traditional disposable, polymer based, flexible materials that are traditionally used with infusion pumps.

While several embodiments have been described in detail, it will be apparent to those skilled in the art that the disclosed embodiments may be modified. Therefore, the foregoing description is to be considered exemplary rather than limiting.

What is claimed is:

1. A method for identifying a pump that corresponds with an infusion set including a catheter having a distal end configured for insertion into a patient's body, the method comprising:
   operatively connecting the pump and the catheter via a tube external to the patient's body;
   operatively disposing at least one sensor on the pump and in operative communication with the tube;
   intentionally generating at least one of a vibration or pressure pulse within or along the tube external to the pump;
   automatically triggering an alarm at the pump in response to the at least one sensor receiving the at least one of the vibration or the pressure pulse transmitted within or along the tube; and
   identifying the pump based on the triggered alarm.

\* \* \* \* \*